United States Patent [19]

Silver et al.

[11] Patent Number: 4,925,924

[45] Date of Patent: May 15, 1990

[54] BIOCOMPATIBLE SYNTHETIC AND COLLAGEN COMPOSITIONS HAVING A DUAL-TYPE POROSITY FOR TREATMENT OF WOUNDS AND PRESSURE ULCERS AND THERAPEUTIC METHODS THEREOF

[75] Inventors: Frederick H. Silver, Bangor, Pa.; Richard A. Berg, Lambertville, N.J.; charles J. Doillon, Edison, N.J.; Arkady Chernomorsky, Elizabeth, N.J.; Robert M. Olson, Princeton, N.J.

[73] Assignee: University of Medicine and Dentistry of New Jersey, Newark, N.J.

[21] Appl. No.: 113,547

[22] Filed: Oct. 26, 1987

Related U.S. Application Data

[63] Continuation-in-part of Ser. No. 843,828, Mar. 26, 1986, Pat. No. 4,703,108, which is a continuation-in-part of Ser. No. 593,733, Mar. 27, 1984, abandoned.

[51] Int. Cl.$^5$ ............... C08F 220/32; A61K 39/385; A61K 15/00; G01N 33/54
[52] U.S. Cl. .............................. 530/356; 514/2; 514/21; 514/801; 424/499
[58] Field of Search ............... 530/356; 514/2, 21, 514/801; 424/489, 499

[56] References Cited

U.S. PATENT DOCUMENTS

| | | | |
|---|---|---|---|
| 4,233,360 | 11/1980 | Luck et al. | 530/356 |
| 4,424,208 | 1/1984 | Wallace et al. | 530/842 |
| 4,841,962 | 6/1989 | Berg et al. | 530/356 |

FOREIGN PATENT DOCUMENTS

| | | |
|---|---|---|
| 0172710 | 2/1986 | European Pat. Off. |
| 1144552 | 3/1969 | United Kingdom |

*Primary Examiner*—John Kight
*Assistant Examiner*—Nathan M. Nutter
*Attorney, Agent, or Firm*—Weiser & Stapler

[57] ABSTRACT

A therapeutic method for treating pressure ulcers like decubitus ulcers with biodegradable collagen flake compositions and with biodegradable collagen sponge or sponge-like compositions. The products of the invention includes biodegradable collagen flake compositions and biodegradable collagen sponge or sponge-like compositions. The products are useful for medical applications, like skin reconstruction, treatment of wounds, especially deep wounds, also in connection with surgery, including cosmetic surgery. The invention also deals with biocompatible synthetic resin sponge or sponge-like and flake products for medical and similar applications. The invention contemplates the treatment of human and animal species.

23 Claims, 4 Drawing Sheets

BAR = 1 cm

COLLAGEN FLAKE

BAR = 1000 μm

BAR = 100 μm

COLLAGEN SPONGE

COLLAGEN POWDER

BAR = 100 μm

BAR = 100 μm

BIOCOMPATIBLE SYNTHETIC AND COLLAGEN COMPOSITIONS HAVING A DUAL-TYPE POROSITY FOR TREATMENT OF WOUNDS AND PRESSURE ULCERS AND THERAPEUTIC METHODS THEREOF

This patent application is a continuation-in-part application of pending U.S. application Ser. No. 843,828, filed Mar. 26, 1986, now U.S. Letters Patent 4,703,108 to be issued Oct. 27, 1987, which patent application in turn is a continuation-in-part application of now abandoned patent application Ser. No. 593,733, filed Mar. 27, 1984.

The specification and disclosure of the two aboveidentified patent applications are incorporated herein by reference in their entirety.

All the prior art to which reference has been made in the prior applications is explicitly referred to herein. In addition, a listing of the publications including patents, which are of interest and representative of the state of the art, appear further below.

THE INVENTION

The invention relates to the field of wound treatment, particularly epidermal and skin wounds, more especially pressure ulcers, like decubitus ulcers with spongelike collagen compositions. The invention is of particular importance for the treatment of patients suffering from such ulcers.

The invention also relates to a collagen-type product, particularly a new collagen flake product, also especially useful for treatment of human pressure skin ulcers, like decubitus ulcers.

The invention also provides a therapeutic method for treating epidermal and skin ulcers especially of humans, which comprises periodically treating the wound with a collagen flake product of the invention. The flake product of the invention need not be of a cross-linked collagen.

The invention also deals with a therapeutic method for treating pressure ulcers with improved sponge-like, cross-linked collagen products which preferably contain fibronectin (FN) and/or hyaluronic acid (HA).

The invention provides a method for treating deep animal dermal wounds or pressure ulcers, especially human decubitus ulcers by treatment with a cross-linked collagen matrix or type I collagen sponge, or with a new collagen flake product.

The invention provides further biocompatible synthetic polymeric materials for wound treatment such as pressure ulcers, with sponges and flake products.

The invention provides therapeutic methods for the treatment of dermal wounds with such biocompatible synthetic materials to promote healing and form new tissue.

The invention provides various useful products for such purposes.

The invention provides a method for promoting optimum tissue ingrowth implants.

The invention provides these various materials, products, methods of treatment and other aspects further disclosed herein for treatment of warm-blooded animals, mammals, especially humans but also for animals of the equine, canine, bovine, and other species. Of course the more important and serious needs are for human patients The invention also provides products useful in fields of application other than wound repair, tissue reconstruction, implants and the like but also in cosmetic surgery.

The invention also provides tissue, skin, etc., materials which have all the characteristics of human or animal living tissue for applications inside wounds, or outside of the body, and applications where all the normal tissue-like characteristics are desired to be simulated.

The invention provides several new products and compositions, and makes available methods of treatment which are a significant contribution to the medical and healing arts.

Other objects and purposes of the invention will become apparent to one skilled in the art from the disclosure which follows.

THE PROBLEM

The invention deals principally with an important problem of pressure ulcers. This problem is assuming increasingly greater importance because of the growth of our aging population and because there is no satisfactory method or product available for dealing with the problem of pressure ulcers.

From the published literature it can be seen that collagen-based materials such as sponges, sheets, sutures and coatings have been used in animal and human studies as dermal dressings and implants because of its biocompatibility and because the collagen-based material has been demonstrated to provide what has been called a "scaffold" for tissue ingrowth and to play an active role in tissue organization during repair.

The work that has been carried out on various wounds has been stymied when collagen products have been used to enhance wound healing on patients with pressure ulcers. With such ulcers the rate and/or extent of healing has not yet been found to be adequately satisfactory to satisfy medical standards. Pressure ulcers are probably one of the most difficult wounds to treat and heal.

The problem occurs frequently with patients subject to prolonged bedrest like quadriplegics and paraplegics who suffer skin loss due to the effects of localized pressure. The resulting pressure sores, also known as decubitus ulcers, exhibit dermal erosion and loss of the epidermis and skin appendages.

It has now been discovered that the healing of decubitus ulcers in stage 2, 3 and/or 4 can be promoted in accordance with the invention. The diagnosis and classification of the stage of an ulcer does overlap to some extent so that at any determined time an ulcer may be in one or more stages. Though ulcers in any of the discussed stages can be treated, presently the treatment is more commonly performed on ulcers in stages 2 and/or 3. Ulcers are traditionally referred to as stage 1 and/or 2 ulcers when the superficial skin layer has been traumatized, abraded and removed (approximately to a depth of 0.1 mm) and where the lesion has progressed to form a wound that can be 5 to 6 or more centimeters (cm) deep and up to approximately 13 cm wide and several cm long. Such wounds also typically show an edge of the skin which has separated from the skin in a flap-like shape.

Traditionally, by medical standards, ulcers have been identified and classified as follows:

Stage 1: loss of epidermis
Stage 2: loss of epidermis and upper layer of dermis
Stage 3: loss of epidermis and dermis Stage 4: exposure of underlying muscle, tendon and bone.

Because pressure ulcers are probably one of the most difficult wounds to repair or heal, the collagen products used in this invention are also useful in the treatment of other wounds generally easier to treat.

BACKGROUND OF THE INVENTION

Figures 1A, 1B, 1C:
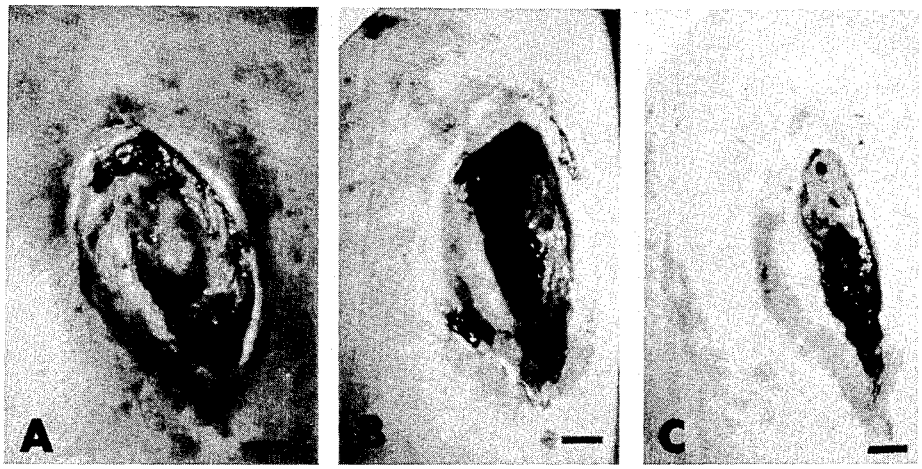
FIG. 1A shows a wound of a patient suffering from decubitus ulcer.
FIG. 1B shows the wound after 3 weeks of treatment with a collagen flake composition of the invention.
FIG. 1C shows the wound after 6 weeks of treatment with a collagen flake composition of the invention.

Thermal, chemical and mechanical trauma to skin results in excessive skin loss and even death. Skin loss if followed by bacterial invasion and ca lead to systemic infection in patients with excessive skin loss or compromised immunological systems. Therefore it is important that new therapeutic methods be developed to enhance the rate of and the extent of healing chronic wounds.

As described in the literature cited herein, repair of large open wounds involves several events including cellular migration, biosynthesis of connective tissue components and other factors, deposition and remodeling of granulation tissue. The remodeling phase has been shown to be accelerated in the presence of type I collagen porous matrix.

It is well known that components of the extra cellular matrix are able to induce cell mobility and attachment. Type I collagen attracts fibroblast in cell cultures and appears to cause directed migration of cells. Fibronectin is known to increase chemoattraction and spreading of fibroblasts in vitro, and is found in large amounts in dermis during embryonic skin development and in healing wounds. Hyaluronic acid is found in high concentrations during embryonic development, is associated with cell movement and differentiation and is the first connective tissue glycosaminoglycan to appear in the extracellular matrix during wound repair.

In addition to high molecular weight components, a variety of low molecular weight cellular products have been shown to stimulate proliferation and enhance cellular biosynthesis of connective tissue components. These factors include epidermal growth factor, platelet derived growth factor, fibroblast growth factor, eye-derived growth factor and cartilage-derived growth factor. Heparin has been shown to induce the formation of capillaries.

Previous work has shown that type I collagen sponges enhance the healing of excised wounds in an animal model.

For a more detailed description of the work above referred, reference is made to the literature cited herein below.

Studies undertaken in conjunction with this invention have involved the analysis of the effects of type I collagen, fibronectin (FN) and hyaluronic acid (HA) on the biomedical and morphological characteristics of fibroblasts and epidermal cells cultured on type I collagen substrates in vitro.

The interest in the studies was to enhance the healing of chronic wounds using connective tissue macromolecules, growth factors and cells to reconstitute synthetic dermal and epidermal replacements. The work focused on the interaction of fibroblasts and epidermal cells with type I cross-linked collagen sponge in vitro cell cultures.

For a better understanding of the work involved in the invention, reference is made in addition to the other references referred to herein, to *Molecular Cell Biology*, Darnell, Lodish and Baltimore, Scientific American Books, Inc., 1986, *Principles of Cellular Organization and Function*, (pages 178-180) which are incorporated herein by reference; *Synthesis and Assembly of Collagen*, (pages 973-1974) which describe how collagens are synthesized by fibroblasts, which are cells localized in interstitial spaces that surround other cells and tissues. The discussion of the role of fibronectin (page 592) and the chapter on *Synthesis of Collagen* and the references there identified (page 983) are also incorporated herein by reference.

In the explanation of the invention the following definition will also be helpful.

"Natural insoluble collagen" as used herein means and refers to collagen which cannot be dissolved in an aqueous acidic or alkaline or in any inorganic salt solution without chemical modification and includes hides, splits, and other mammalian or reptilian coverings. More particularly, "natural insoluble collagen" means and refers to the corium which is the intermediate layer of a bovine hide between the grain and the flesh sides.

Collagen constitutes the connective tissue and is the major type of fibrous protein in higher vertebrae. Collagen in its natural state exists in a triple chain helix along with a constant periodicity between aligned triple chains. The triple helical configuration of collagen is sometimes referred to as a rod and a group of molecules align themselves with an axial periodicity of about 640 Å.

Although there are several types of collagen, the major type is referred to as "type I" which is the major collagen of skin, bones and tendons. Type I collagen has a chain composition of [alpha 1 (I)$_2$ alpha 2 (I)]. The alpha 1 (I) and alpha 2 (I) chains are homologous.

It is also contemplated that the flake and sponge products be included in the invention when made from types of collagens other than collagen type I, for instance types II, which corresponds to [alpha (II)]$_3$; type III which corresponds to [alpha I (III)]$_3$; type V which corresponds to [alpha I (IV)]$_3$ and [alpha 2 (IV)]$_3$ and type V which corresponds to [alpha I (V)]$_2$ alpha 2(V). Type I is principally distributed (as noted above) in tissue like skin, tendon, bone, dentin and fascia; the other types are distributed in cartilage, notochord, vitreous body; skin uterus, blood vessels, "reticulin" fibers; kidney glomeruli, lens capsule; basement laminae of smooth and striated muscle cells; exoskeleton of fibroblasts and other mesenchymal cells. The different types of collagen are built of different but related collagen polypeptides The chains differ in the extent to which their proline, lysine and cysteine residues are modified. See, *Characteristics of Different Types of Colla-* gen, in Darnell, above cited (page 179, Table 5-6), also included herein by reference. Presently because of the greater ease of extraction and purification of collagen Type I, that type is more commonly used.

In young animals there is little intermolecular and interfibrilar cross-linking which provides for some degree of solubility of the collagen. However, during the aging process both intermolecular and interfibrilar cross-linking occurs, thus making the collagen insoluble.

Certain of the materials and methods used in conjunction with this work have been disclosed in the literature referred to herein. Scanning electro microscope (SEM) or light micrographs studies have been conducted on collagen sponges to determine the factors that influence pore size and matrix configuration. (See references 4 and 5).

DESCRIPTION OF THE INVENTION

The manufacture of a collagen product which is acceptable for medical and commercial purposes from all important points of view has not yet been satisfactory accomplished.

An objective of this invention is to provide such products and a reliable method for making such products. Many variables have been considered and tried by workers in the prior art; none, as far as could be determined, found the set of conditions which yielded reliably a satisfactory product.

In accordance with this invention, optimum conditions have been established for manufacturing a collagen product, e.g. a sponge, which to date is most satisfactory. The process comprises dispersing a finely divided inorganic acid like hydrochloric acid at a pH preferably between about 1.0 and 4.0, even more preferably from about 2.0 to about 3.75. The collagen is preferably in concentrations of about 0.5 to about 1% weight/volume. The temperature at which the operations are performed is in the range of about 15° to 35° C., preferably 20°-30° C. A temperature of 22°±2° C. has been observed. The dispersing or blending is performed with any suitable mechanical blending means such as a stirrer (Osterizer Blender), for a time sufficient to accomplish a thorough dispersion. Preferably the dispersion is then deaerated under appropriate vacuum like less than 0.4 millitorr.

The collagen dispersion is then frozen under conditions conducive to obtain a fibrous structure which contains pores, ideally of substantially uniform average pore size, preferably of about 100±50 um and containing channels connecting the exterior of the sponge to the inside, generally connecting one side of the product to the other, and pores that open into the channels. To obtain a very satisfactory product, the collagen dispersion is freeze-dried at a temperature range of about −20° to −35° C., preferably at about −30° C. in a bath of a lower alkanol, like ethanol. Preferably air gaps between the sponge body and the container are minimized.

Various freezing conditions were tried from about −20° C. to −90° C. using an ethanol bath containing dry ice or liquid nitrogen, or other appropriate means. The frozen product (generally about at least 2 hours) is then dried, conveniently in a chamber pressure of about 0.1 millitorr at a temperature of −60° C.

When it is desired to have a cross-linked product, such as a sponge, cross-linking can be performed by any method known in the art. Preferably, cross-linking is performed in accordance with a two-step process resulting in formation of peptide bonds on oppositely charged side chains. See K. Weadock, R. M. Olson, F. H. Silver, Evaluation of Collagen cross-linking techniques. *Biomater. Med Denies Artif. Organs,* 11, 293–318 (1984), (reference 35) which is incorporated herein by reference.

The cross-linking may also be performed as disclosed in the parent patent application, referred to above.

The cross-linking methods disclosed herein and in the parent patent application result in a stable cross-linked sponge with stable pores and channels (which show no skrinkage of the pores or the channels). The products so obtained are sponges which are characterized by a dual porosity, as described further below.

In accordance with another process of the invention, a flake product is made which also has dual porosity as will be described further below.

The products of the invention ideally show a highly fibrous structure associated with an average pore size of about 100+50 um containing channels which offer an ideal structure for a collagen-based material for tissue ingrowth as needed for an "artificial" dermis. Fibroblast behavior does, it has been noted, have a relationship to pore size; tissue ingrowth into the porous sponge occurs when the pore size is between about 50 to 300 um, ideally when pore size is about 80 to 120, often about 100 um.

The collagen flake product of the invention may be described as follows.

The product comprises collagen flakes generally non-uniform in size, length and thickness. The fibers are organized or positioned randomly in a plane generally horizontal. The flakes define between them non-uniform channels some of which extend throughout the product from the surface deep into the interior, or cross the entire product and form a labyrinthal-type structure. The collagen flakes also have interconnecting pores, the pores having openings into the channels. The flake product of the invention can have a large proportion of channels communicating with the pores, a proportion of the pores though interconnecting with each other do not all open into the channels. The dual type of porosity (channels and pores) and flake-like structure has an enhanced beneficial and healing effect on the wound.

Described in greater detail, the morphology of the flake product shows a network of individual collagen fibers, generally at least about 1 um in diameter forming a web-like mesh, as well as an aggregate of collagen fibers which appear to form a sheetlike structure with channels between the individual collagen fibers and between the sheets of collagen fibers. The channels connect surface pores and pores in the interior of the sponge. The collagen fibers contain pores the greatest majority of which (at least 50%, generally over 80% or 90% by volume), are interconnecting with each other; and a significant proportion of the pores, e.g., 50 to 80%, connect to the channels.

Since the flakes are constituted of the collagen fibers, it is evident that the flakes can be as long as the fibers; the thickness of the flake can also vary but will generally be less than the length or width of the flake.

Figure 3:
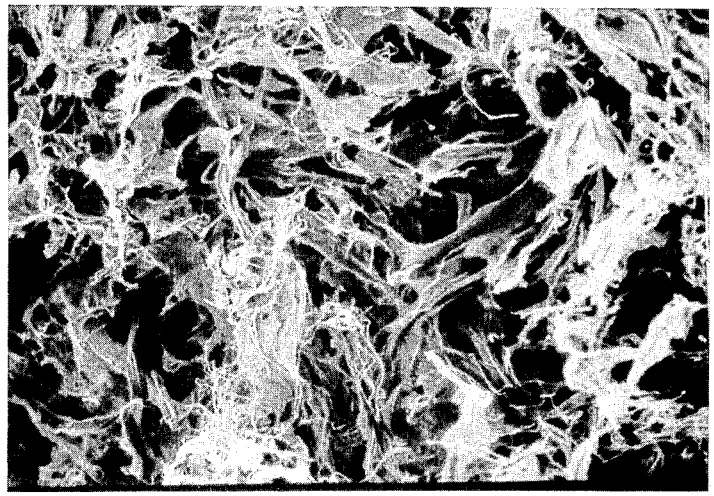
FIG. 3 shows a flake product of the invention (Bar 1000, μm).
Figure 2:
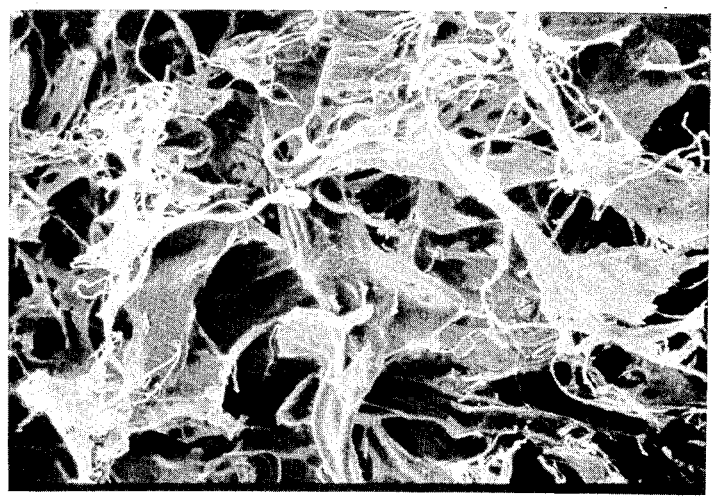
FIG. 2 shows a flake product of the invention (Bar 100, μm).
Figure 4:
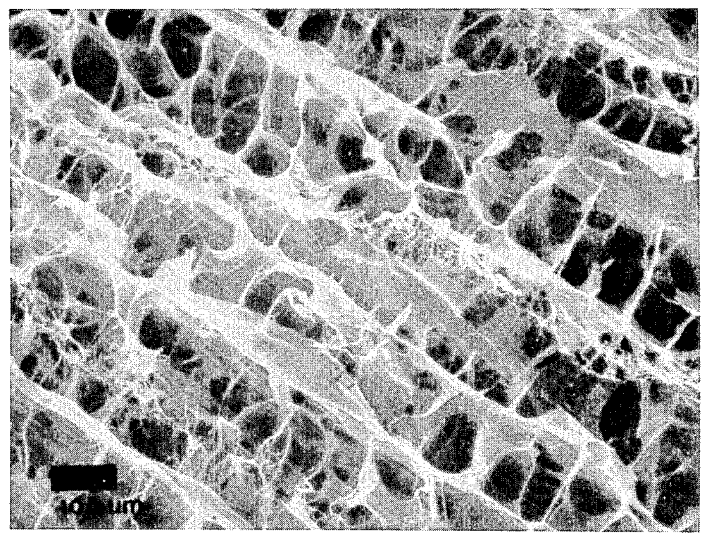
FIG. 4 shows a sponge product of the invention (Bar 100, μm).

A typical morphology of a flake product of the invention is seen in FIGS. 2 and 3.

An illustration of a sponge product is seen in Doillon et al, Collagen based wound dressing: Control of the pore structure and morphology (FIGS. 1, 2, 3 and 4 in Ref. 5).

In a cross-sectional view, the channels of the flake product of the invention appear cylindrical or spherical. Ideally, the pores are generally uniform in average diameter, preferably between 5 to 300 μm, ideally from about 20 to 110 μm, even better about 30 to 75 i.e., about 50 μm. From diffusion studies it has been observed that no channel is so small as to exclude a macromolecule up to 100,000 in molecular weight.

The collagen flake can vary in length often between about 0.1 to 3 cm, commonly about 1 cm. The type of application or use influences the type of collagen product best suited for the application. For large wounds, it is acceptable for the flake of the flake product to be longer than for small wounds.

It is evident that the flakes of the product of the invention can be longer than the individual fibers themselves since the fibers often, if not generally, will align themselves length-wise partially or totally overlapping other fibers, to form the flake (or mat-like structures) of the invention.

The flake products of the invention have a surface area which is markedly greater than that of collagen sponges, often from about 20% to at least 50% or even to about 80% greater than that of sponges.

The flake products of the invention may or may not be of cross-linked collagen; both types are acceptable. The sponge product used in the invention is preferably cross-linked, and most preferably contain FN and/or HA. The preparation of collagen products with HA and/or FN is disclosed in the parent application which is in that respect also incorporated by reference.

With respect to the flake product of the invention in vivo studies have not yet clearly shown whether the presence of FN and/or HA in the collagen structure gives a product with distinct enough advantages to justify the additional costs involved. At present it appears that the flake product is so satisfactory that the addition of FN and/or HA would appear not to offer distinctive enough advantages for the main applications of the invention.

The flake product of the invention is distinguishable over collagen powders. Contrary to expectations, collagen powders were very unsatisfactory in the principal application of the products of the invention, i.e., as wound dressing. The porosity of powder is virtually of one type of pores; no channels could be observed and the pores were of very small size, in the order of not over about 10 μm, generally 1 to 5 μm. Absorbancy of the fluid of the wound was unsatisfactory; handling of the powder and packing of the would were very difficult. These and other disadvantages are the reasons why a powder product has no practical interest as presently perceived.

The process of the invention for making the flake product of the invention comprises treating a collagen sponge product with shearing means under conditions of minimum pressure. The shearing process cuts slices or lamellae of the sponge with the minimum application of pressure. The dry sponge product is exposed to cutting means that sliced-off pieces or slices or flakes of the collagen sponge and minimizes destroying the porous structure of the collagen. It is preferable in the shearing process that the sliced-off pieces of sponge be removed from contact with the cutting means, or other means that are likely to cause compression of the product. The resulting flake can vary in size from about 0.1 mm to about 1 mm in average thickness. However, the thickness of the flake can be adjusted by adjusting the cutting or shearing means. Multiple shearing blades may be used, in which case the distance separating two such adjacent means determine, at least in part, the thickness of the flake.

The process of the invention therefore comprises causing a shearing strain to be applied to a sponge, the strain resulting from forces that cause or tend to cause contiguous means to slide or move relative to each other in a direction substantially parallel to each other. The shearing stress causes lamellae or slices of the sponge to be cut off the porous body and the body sheared into numerous flakes. The compression stress during (before and after) the shearing is preferably minimal or essentially nil.

Of course multiple shearing means need not be used. The sponge may be advanced toward a shearing means, which will cut off flakes and remove the flakes from contact with the shearing means.

The means for shearing the porous sponge are not critical. Any suitable means which accomplish this purpose is suitable. At the present time a device which is quite satisfactory comprises a container for the sponge which includes sharp propeller-like knives in an elongated tube-like cylinder which allows the sliced-off flakes to be removed upwardly from the vicinity of the shearing means. A Willey mill has been found quite satisfactory. Of course, the device can be made to operate in such a manner that gravity will remove the sliced-off flakes from the vicinity of the blades.

The invention contemplates mechanical means for accomplishing the shearing. Likewise other means which accomplish the equivalent can be used, like ultra sonic devices and the like.

The flake product of the invention need not be made from a porous collagen sponge but may be made directly from the collagen fibers without going through the intermediary of the sponge.

The flake products need not be made of a synthetic biocompatible polymer sponge but can be made directly from the synthetic fibers without going through the intermediary of the sponge.

For instance, the flakes can be formed into mat-like or flake-like structures.

The flake products made of synthetic biocompatible polymers, as described hereinafter, are made in the same manner.

A satisfactory flake product for the purpose of the invention can vary over a wide range. Preferred is a flake product that includes virtually no powder particles (particles which pass a 40 mesh screen) and where the majority i.e., over 50%, preferably over 80% to about 100% of the flakes will pass through a 10 to 30 mesh screen. The fibers are generally 0.1 mm to 3 mm (or more) of average length, often about 1 mm long, or longer as described above. It is understood that considerable latitude is allowed as long as the product is a flake product of the collagen (or of the biocompatible synthetic polymer). Suitable separating means, like a screen, separate the flakes from smaller particles, like powder of sponge.

The conditions under which the shearing process is carried out can vary considerably. The shearing process can be carried out concurrently with, prior to, or following other steps or treatment of the collagen of the invention.

The temperature at which the shearing process is carried out is generally any temperature which will not disintegrate or damage the starting and final product, such as in the range from above freezing to about 60° C., preferably about room temperature. The length of time for which the shearing process is carried out is until the desired flake product is obtained, a flake product having the morphology described above. One skilled in the art can without any undue experimentation adjust the time and speed of the shearing means.

The atmosphere under which the shearing process is carried out can be air, or any other desirable atmosphere. The process may be carried out under vacuum. Preferably the atmosphere is dry air. The atmosphere may be sterile or at least filtered air. The product is preferably sterilized after the shearing process. In an interesting aspect of the process of the invention, the collagen may be cross-linked during the shearing. That is, the collagen may be first freeze-dried and then cross-linked, either prior to, concurrently or subsequently to the shearing process. For instance, in that connection, the atmosphere in the shearing apparatus there may be provided an appropriate atmosphere like vapor of the desired cross-linking agent. For instance, any of the chemicals which have been used in the prior art may be vaporized, such as an aldehyde, carbodiimides and the like and the polymerization may be concurrently carried out (or prior, or after) with the shearing process.

When sterilization is carried out on the product, an appropriate sterilization gas, such as ethylene oxide, may be used.

The process of the invention may be carried out in a batch-like or continuous manner. In either, larger chunks of the product may be separated from the flake product and recycled to be sheared to the appropriate size.

It can be readily seen that the process of the invention lends itself, also when carried out on a commercial scale, to a variety of appropriate adaptions to obtain the desired flake product of the invention.

In accordance with the invention, it is contemplated not only that collagen be used for the product but also there may be used any other biocompatible synthetic polymers. Biocompatible synthetic polymers that are contemplated for the uses disclosed in conjunction with the invention include those described in *Transdermal Controlled Systemic Medications*, Marcel Dekker, Inc., (1987), in the section on Polymeric Materials of Skin Biocompatibility, Kevin S. Weadock et al., which is incorporated herein by reference.

Typical polymers are the polyurethanes, polyethylenes, silicone polymers, hydrogels and others. Polymers which are free of additives used during manufacture are considered least likely to cause allergic or tumorigenic responses. The synthetic polymers may or may not be biodegradable.

It is noteworthy though that such synthetic fibers are obtainable in any length and therefore the flake product can be as long as desired for the particular application. Also, such fibers are generally more uniform in diameter than collagen fibers. Thus the flake product of synthetic fibers of biocompatible polymers offers certain desirable practical features in accordance with this invention.

In a similar manner, the synthetic biocompatible polymers are manufactured as described above, for instance from porous polyurethanes and the like.

In accordance with the invention, it is noteworthy that pores in the collagen sponge (or synthetics) which were interconnected (or not interconnected) but positioned within the interior of the sponge structure now connect to surfaces of the flakes and/or to the channels between the flakes. Thus, the morphology of the products of the invention are typified by this dual porosity and also by a remarkable increase in surface area. This morphology is much more ideal and conducive to attracting fibroblasts and epithethial cells and thereby promoting synthesis of the new collagen in a wound.

Thus the particular morphology of the collagen flake of the invention is virtually ideal as discovered to date to promote the deep healing of the wounds.

Notwithstanding the fairly extensive scientific literature and patents published on collagen and its role in wound and skin repair or "synthetic" skin, as some publications refer to it, it is surprising that no collagen product has been described that has the morphology of the products of the invention; nor has it been appreciated until now that the morphology of the products of the invention can have such beneficial effects on wound healing.

In conjunction with the treatment of wounds with collagen sponge, it has been shown in the parent patent application that HA and/or FN has certain beneficial effects.

In the treatment of ulcers in accordance with the invention, the role of HA or FN should also be taken into account. In the presence of HA, the synthesis of collagen was increased at day 3 post-seeding in comparison to that observed in the presence of FN or collagen sponge alone. In the presence of FN, deposition of collagen into matrix was increased particularly at days 7 and 9 post-seeding in comparison to that observed when cells were grown on collagen sponge alone. Although FN and HA both enhance wound healing in vivo, they both do not appear to influence the healing process in the same manner and at the same time.

Further, from work performed with fibroblasts grown on plastic culture dishes, it could not always be predicted whether extra cellular matrix (ECM) would form in vivo. Cells plated on a collagen sponge were not confluent, but newly synthesized ECM was present. On the collagen sponge, cells were observed to be elongated and had several filopodia extended in all directions attached to the exogenous and newly formed collagen as well as microvilli on the surface facing the medium. No microvilli were observed on cells grown on plastic.

Cells grown on a collagen sponge became confluent at day 6 post-seeding and SEM observation showed this confluence resulted in a superficial layer of cells which prevented observation of the underlying ECM. Microvilli as well as filopodia were observed on cells grown on the collagen sponge. By light microscopy, cell confluence and superposition were observed o the surface when cells were grown on plastic as well as when grown on a collagen sponge. Beneath the layer of confluent cells, ECM associated with round or triangular shaped cells was observed for cells on plastic as well as for cells on collagen. Synthesized collagen deposited into the matrix is higher, and that released into the culture medium is lower, compared with plastic. Collagen synthesis does not decrease as the cells approach confluence.

In the presence of HA or FN, the growth rate and collagen synthesis are increased. This may be explained by increased cell division or by an increase in the number of cells that migrated into the interior of the sponge containing HA or FN when compared to cells grown on the collagen sponge alone.

Another beneficial effect of FN and HA was noted. Prior work had suggested that the replication of fibroblasts may be inhibited by the presence of collagen. It is of interest that the presence of FN or HA either release the cells from this inhibition or themselves stimulate the growth and division.

In accordance with this embodiment of the invention, it was noted that the biochemical composition also influences the infiltration of cells (observed by light microscopy). The presence of FN or HA affected cell infiltration into a collagen sponge. In the presence of HA, cells observed in the porous spaces may be bound directly to HA and not in direct contact with collagen, since HA may be situated within the porous spaces of the sponge. In the collagen sponge, direct contact of cells with HA bound to collagen fibers may allow the cells to proliferate and synthesize ECM in contrast to that observed when cells are in direct contact with the collagen fibers alone. Previous studies suggest that direct exposure of fibroblasts to gel of HA inhibits cellular mobility and multiplication. The results of the work in connection with the invention suggests that the combination of HA and collagen fibers is important in enhancing cellular mobility and replication.

In the presence of FN, cells behave differently. Based on previous SEM observations deposition of ECM appears to occur primarily on the collagen fibers of the superficial layer of the sponge. This observation may correspond to the increased deposition of collagen into the matrix observed by radiolabel techniques at day 9 post-seeding. Only a small amount of newly formed ECM appears to be deposited around cells attached to the collagen fibres of the interior of the sponge. In the collagen sponge, it has been noted that FN may bind directly to collagen fibres and therefore is not situated within the porous spaces of the sponge as is found with HA. FN bound to collagen facilitates cellular infiltration and cell attachment as observed by light microscopy but does not enhance deposition of ECM in the interior of the sponge. Replication and biosynthesis of collagen by fibroblasts appear therefore to be influenced by direct contact with the ECM environment rather than by the structure of the support used.

In conclusion, fibroblasts grown on collagen sponges containing FN or HA proliferate and deposit more newly synthesized collagen into the matrix compared with fibroblasts grown on the unmodified matrix or on plastic. Specifically, HA in the matrix encourages cellular infiltration into the pores and channels of the sponge while FN induces cell attachment to the collagen fibers of the sponge. Incorporation of HA and FN into the collagen sponge enhances cell mobility and replication in the collagen sponge and improves its properties as an artificial connective tissue. Thus, the presence of FN and/or HA sponges in the treatment of pressure ulcers likewise contributes to speedier and improved healing.

As disclosed in the parent application and in the literature, the sponge product used in the invention and the flake product of and used in the invention may contain any number of additives that are conducive to healing the wounds, like hormones, bactericides and growth promoters, immunogens, antibiotics and the like.

The following examples and illustrations are not intended to be a limitation on the invention, but are intended and are merely illustrative. One skilled in the art will readily be able to make variations in the various procedures illustrated below without departing from the spirit of the invention.

MATERIALS AND METHODS

Collagen Sponge Preparation

Collagen sponges were prepared for cell culture studies and human studies as described previously (Doillon et al., 1984). Type I collagen from cow hide was dispersed at 0.5% (W/V) in HCl solution (pH 3.0), freeze-dried and crosslinked according to Weadock et al., (1984). Collagen sponges were sterilized by exposure to 2.5 M rads of gamma irradiation.

Fibronectin (FN) was extracted from fresh bovine blood as described by Ruoslahti et al., (1982) and was found by polyacrylamide gel electrophoresis to be composed of two polypeptide chains with a molecular weight of about 220,000 after reduction (Brokaw et al., 1985). FN was dissolved in 0.1 M ammonium acetate.

Hyaluronic Acid (HA) from Sigma Chemical Co. (grade III; potassium salt) was used and dissolved in HCl solution (pH 3.0). FN and HA solutions were mixed with the collagen dispersion in a Waring blender. Mixtures containing weight ratios of 1:99 FN to collagen and 1:19 of HA of collagen were prepared. Tissue ingrowth was maximized with these concentrations of HA and FN (Doillon and Silver, 1986a).

Sponges can also be prepared in accordance with the method shown in the above referenced pending patent application. Appropriate methods are also disclosed in Doillon et al (References 3, 4, 5 and 6).

Cell Cultures

Fibroblasts were grown on collagen sponges after the sponge pH was stabilized by immersion in serum-free Dulbecco's Modified Eagle Medium (DMEM) (Gibco Laboratories) for three days. Fibroblasts were derived from embryonic chick tendons as described by Kao et al (1975) and cultured in DMEM supplemented with 100 units/ml penicillin, 100 ug/ml streptomycin, ascorbic acid (10 ug/ml added daily) and 5% fetal bovine serum (FBS) (Gibco Laboratories). Fibroblasts were plated as primary cultures at concentrations of $1.5 \times 10^5$ to $3.2 \times 10^5$ cells/cm$^2$. To seed the sponges, cells were suspended in 50 to 250 ul of DMEM and the mixture spread on each sponge and allowed to attach for 2 hrs (Doillon et al., 1987). Cells were grown at 37° C., in a tissue culture incubator in a 10% CO$_2$ atmosphere. The medium was changed every 2 days and fresh ascorbate added daily.

Epidermal cells were obtained from pieces of guinea pig skin that were excised, defatted and cut into 1 mm$^2$ pieces (Doillon et al., 1986c). The pieces of skin were washed in culture medium composed of a 1 to 1 mixture of DMEM and Ham's F 12 Medium (F12) (DMEM/F12; supplied by Sigma Chemical Co.) containing 100 ug/ml of penicillin, 10 ug/ml streptomycin and 3 ug/ml of amphotericin B. Pieces of skin were then placed in a DMEM/F12 solution containing 5 mg/ml of collagenase (Copper Biomedical) for 90 minutes. The digested skin pieces were then sedimented for 10 minutes under gravity. The sediment rich in epidermal cells were suspended, counted and used for seeding.

Epidermal cells were cultured in DMEM/F12 supplemented with antibiotics, insulin (1 ug/ml, hydrocortisone (20 ug/ml) and 15% FBS (Doillon et al., 1986c).

Cells were plated as primary cultures at a concentration of $2 \times 10^6$ cells/cm$^2$. Cells were seeded on each collagen sponge as described for fibroblasts. After 2 hours, the remaining culture medium was added. Cells were grown at 37° C., in a tissue culture incubator in a 5% $CO_2$ atmosphere. The medium was replaced every 2 days. The FBS was decreased from 15% to 10% over a one week period.

Other methods disclosed in the referenced publications may also be used and are made part hereof by reference.

Radiolabeling Experiments

Fibroblast cultures were labeled at days 1, 3, 5, 7 and 9 post-seeding using DMEM containing either 2 uCi/ml [$^3$H] thymidine or 2 uCi/ml [$^{14}$C] proline (New England Nuclear). The labeling medium contained 10 ug/ml ascorbate. Fibroblasts were incubated with [$^3$H] thymidine for four hours. The medium was removed, a 0.5 N perchloric acid solution added and cells were collected as previously described (Doillon et al., 1987). After sonication, the precipitated DNA was washed two times with 0.5 N perchloric acid and heated at 90° C. for 90 minutes. After centrifugation, the supernatant was counted in a liquid scintillation counter (Aquasol-2, New England Nuclear).

Other fibroblast cultures were incubated with 2 uCl/ml [$^{14}$C] proline for four hours. The medium was then separated from the cells and fresh DMEM was added to the cells. Cell and medium fractions containing radiolabeled [$^{14}$C] proline were treated and protease inhibitors (Kao et al., 1977) and sonicated. The samples were brought to a final concentration of 2% sodium dodecyl sulfate (SDV), dialyzed against SDS sample buffer containing 2% (W/V) SDS, 10% (V/V) glycerol, 0.005% bromophenol blue in 0.124 Tris-HCL ph 6.8, and an aliquot was counted in a liquid scintillation counter.

Epidermal cell cultures were labeled between days 15 and 22 using the methods described for the fibroblast cell cultures (See above).

Light Microscopy

Primary cell cultures were observed 9 days post-seeding. Collagen-based sponges and plastic dishes seeded with cells were washed briefly with phosphate buffered saline solution then fixed with modified Karnovsky's fixative. Specimens were embedded in glycol methacrylate as described previously (Doillon et al., 1984). Control plastic dishes containing cells were treated in a similar manner for light microscopy. Light micrographs were taken with a Laborlux 12 Pol light microscope equipped with a 35 mm camera at a magnification of 128X.

Human Studies

The protocol for in vivo studies was as follows. All patients suffered from severe decubitus ulcers. A patient consent form was signed by all subjects.

Sterilized collagen flakes were applied to non-infected dermal ulcers ranging from about 1 to 10 cm$^2$ in surface area. Only ulcers classified as stages 2 or 3 were used in this study. The degree of subcutaneous erosion varied from patient to patient but in no case was the material placed over exposed tendon, muscle or bone (stage 4). The patients ranged in age from about 35 to 70 years of age. At least 6 patients were studied in the control and collagen treated groups.

Both control and collagen treated wounds were cared for using the protocol that follows. All wounds were washed with a 1% (W/V) solution of hydrogen peroxide followed by normal saline. The collagen flakes were then packed into the wound (except for controls). All wounds were then covered with saline wetted cotton gauze. A layer of dry cotton gauze was then applied and taped to surrounding healthy skin. All wounds were washed with hydrogen peroxide and saline and rebandaged daily. Wounds treated with the collagen flakes were repacked daily after wounds were washed with saline.

The rate of dermal wound healing was estimated by photographing the wound once a week and tracing the wound perimeter using a plastic transparency directly laid over the wound. Wounds were photographed from a constant distance with a ruler placed next to the wound. The wound area was calculated using a digitizing pad interfaced with an IBM PC. Wound areas were normalized by dividing by the original wound area (time=0) to yield a value of % area change.

Results And Discussion

Previous studies indicate that type I collagen sponges enhance repair of animal dermal wounds by organizing the spatial deposition of newly synthesized collagen and accelerating remodeling. In addition, incorporation of hyaluronic acid and fibronectin into a type I collagen sponge results in increased numbers of fibroblasts that migrate into the collagen-based sponge and consequently an increased deposition of newly synthesized collagen is observed.

Observations by SEM of freeze-dried collagen samples show a porous structure with pore sizes generally between 60 and 250 um of structure, defined by SEM, which appear either superficial without connection with deep layers ('superficial pores') or with connections to the deep structure of the sponge ('deep pores') which are termed 'channels'. Superficial pores were frequently found in the presence of 5% FN and 1% HA, in a few cases superficial pores were found in the presence of 1% HA+1% FN. Deep pores are frequently observed in the presence of 1% HA+1% FN, but also within the control collagen sponge and in the presence of 1% HA. Channels or deep pores are smooth on their inner surface in almost all cases and particularly in the presence of 1% FN. Formation of fibrous structures is observed on the surface of deep or superficial pores in the presence of 1% HA+1% FN, and 5% HA+1% FN; the lowest frequency is in the presence of 5% HA.

The deep pores or channels are generally interconnecting forming a labryinthal-like structure; not all channels are interconnecting and not all channels have openings to the exterior.

In all cases, plastic embedded sponge sections showed a porous structure of pores varying from about 20 to 200 um. Channel structure was regularly observed when HA and FN were both associated at 1% with collagen. In the latter case, "open" channels were frequently seen with large interchannel connections.

The interaction of fibroblasts and epidermal cells with collagen sponges in a simple cell culture model as well as in a more complicated human dermal ulcer is described below.

Fibroblasts grown on plastic adopt a flattened shape and synthesize some extracellular matrix (ECM) (see Table 1). In comparison, cells grown on a collagen sponge form several confluent layers of elongated cells and deposit a large amount of ECM. However, by day 9 only about 25% of the collagen sponges are infiltrated with fibroblasts. Fibroblasts grown on collagen sponges containing 5% (W/W) hyaluronic acid are found throughout the collagen sponge primarily in pores that are formed by the collagen fibers of the sponge. Fibroblasts grown on collagen sponges containing 1% (W/W) fibronectin were observed to be attached and elongated along the collagen fibers and infiltrated throughout the sponge. In the presence of hyaluronic acid or fibronectin several superficial layers of confluent cells are seen on the surface of the collagen sponge.

Fibroblasts grown on plastic for 3 days in cell culture incorporated about five times more of [$^{14}$C] proline counts (collagen synthesis) than were incorporated into cells grown on a type I collagen sponge. This result suggests that the presence of a collagen matrix inhibits collagen synthesis by fibroblasts. [$^3$H] thymidine incorporation (cell replication) into fibroblasts after three days in cell culture was similar for cells grown on plastic and on a collagen sponge; however, [$^3$H] thymidine incorporation was increased by the addition of 5% HA or 1% FN. By day 9, these trends were still present (see table 2) although the differences were less noticeable. Fibroblasts grown on all substrates synthesized type I procollagen, type I collagen and several processing intermediates based on [$^{14}$C] proline incorporation and fluorography. The results suggest that the interaction between a porous type I collagen substrate and fibroblasts leads to inhibition of collagen production. Cell replication and collagen synthesis can be increased by addition of small amounts of HA or FN such as 0.1% to 5.0%. Larger amounts e.g., 10% do not seem to have the desired effect.

Collagen synthesis and cell replication were evaluated for epidermal cells grown on a type I collagen sponge (see table 4). Epidermal cells formed more layers of stratified cells when grown on collagen than when grown on plastic. Tight packing of cells on the sponge surface was observed which was not observed when these cells were grown on plastic. In the presence of a collagen sponge some cultures showed evidence of a basement membrane-like structure between the collagen sponge and a layer of basal cells. In addition, in the interior of the collagen sponge, epidermal cells formed clusters that resembled primitive glands. However, as indicated by the results listed in table 4 the collagen sponge did not inhibit incorporation of [$^{14}$C] labeled proline into collagen. These results suggest that a type I collagen sponge seems to encourage basement membrane deposition (type IV collagen and laminin) by epidermal cells.

Results of cell culture experiments suggest that both fibroblast and epidermal cells replicate and synthesize collagen when grown on a type I collagen matrix. The collagen matrix inhibits collagen synthesis by fibroblasts but appears to be highly biocompatable with both fibroblasts and epidermal cells. The biocompatability of this collagen matrix and the chemotactic properties of collagen derived peptides suggests that a collagen matrix may be useful in enhancing healing of chronic wounds such as decubitus ulcers. See Tables 3 and 4.

The results of these in vitro tests were not conclusive enough to be able to foresee the results of the use of collagen sponges in the treatment of such deep wounds as decubitus ulcers.

In Vivo Treatment

Patients treated with a standard protocol that included daily irrigation of the wound and gauze bandaging exhibited no decrease in wound area over a 6 week period. In many cases the wound area remained constant for three or more months. When the protocol for treatment of these patients was modified to include packing the wound daily with a type I collagen flake, the wound area decreased by an average of 20% in three weeks and 40% in six weeks. After three weeks of collagen treatment the wounds show increased blood supply based on their color and by six weeks significant epidermal migration is observed.

The results show that the rate of wound healing of decubitus ulcers (stages 2 and 3) is enhanced by daily treatment with type I collagen flakes. The mechanism of the enhancement appears to involve attraction of dermal and inflammatory cells into the wound area.

Treatment of an ulcer in stage 4 is carried out in like manner. Healing of the wound to stage 2 and 3 and then stage 1 was observed. Treatment takes longer in view of the severity of the wound.

Generally no occlusive dressing is used except for wounds in stage 1.

In therapy with collagen sponge, about 50% of patients showed some improvement while about 50% showed no improvement. In the therapy with flakes all patients showed improvement.

Figure 5:
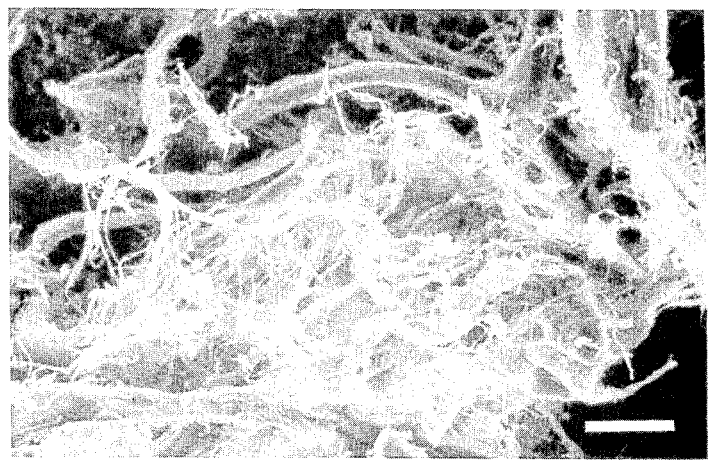
FIG. 5 shows a powder product of the invention (Bar 100, μm).
Figure 6:
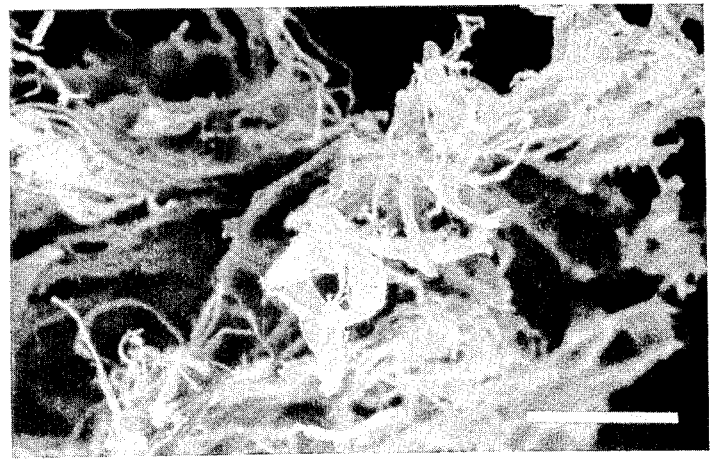
FIG. 6 shows a powder product of the invention (Bar 100, μm).

| FIGURE LEGENDS | |
| --- | --- |
| FIG. 1A | Photograph of a decubitus ulcer on a patient. |
| 1B | Photograph of same ulcer after 3 weeks treatment with a flake product of the invention. |
| 1C | Photograph of the wound after treatment with the flake product for 6 weeks. The wound shows a gradual closing, evidence of new tissue and blood circulation. Controls (not shown) did not change in their appearance in 3 and 6 weeks. Both controls and collagen treated ulcers were irrigated and packed daily. |
| FIG. 2 | Scanning electron micrographs showing collagen flake intermeshed network; the flakes are randomly organized with no discernable pattern. Channels of varying length, diameter and structure run through the flakes. The channels are interconnecting bands of lesser proportion do not interconnect. The flakes are random in length and width, generally about 0.5 to 1.5 mm, often about 1 mm in thickness. The pores in the flakes range in diameter from about 5 to about 10 $\mu$m; the channels from about 100 to 1,000 $\mu$m. Bar. 100 $\mu$m. |
| FIG. 3 | Scanning electron micrographs showing collagen flake intermeshed network; the flakes are randomly organized with no discernable pattern. Channels of varying length, diameter and structure run through the flakes. The channels are interconnecting bands of lesser proportion do not interconnect. The flakes are random in length and width, generally about 0.5 to 1.5 mm, often about 1 mm in thickness. The pores in the flakes range in diameter from about 5 to about 10 $\mu$m; the channels from about 100 to 1,000 $\mu$m. Bar. 1,000 $\mu$m. |
| FIG. 4 | Scanning electron micrographs showing a sponge used with the invention. The pores in the fibers and the channels between the fibers are apparent. Bar shown 100 $\mu$m. |
| FIGS. 5 and 6 | Scanning electron micrographs showing a powder of porous collagen. The product is seen to be porous; the pores appear to be of only several microns; virtually no channels are apparent. The physical integrity of the structure is largely destroyed. Bar shown 100 $\mu$m and |

-continued

FIGURE LEGENDS

100 μm, respectively.

TABLE 1

9-Day Fibroblast Cell Culture Experiments-Morphological Results

| Substrate | Observation |
|---|---|
| plastic | 1. superficial layers of confluent cells<br>2. formation of multiple cell layers of rounded or triangular shaped cells<br>3. formation of some ECM* |
| collagen sponge | 1. superficial layers of confluent cells<br>2. elongated superficial cell layers<br>3. presence of ECM* throughout ¼ of sponge |
| collagen sponge + 5% hyaluronic acid | 1. superficial layers of confluent cells<br>2. 1 high degree of cell infiltration throughout the sponge<br>3. rounded and triangular-shaped cells surrounded by ECM* sseen in pores |
| collagen sponge + 1% fibronectin | 1. superficial layers of confluent cells<br>2. moderate cell infiltration throughout sponge<br>3. fibroblasts appear to attach to and elongate along fibers of sponge |

*ECM = Extracellular Matrix

TABLE 2

9-Day Fibroblast Cell Culture Experiments-Protein and DNA Synthesis Results

| Substrate | [$^{14}$C] proline CPM** on substrate mean ± SEM* | [$^{14}$C] proline CPM** in medium mean ± SEM* | [$^{14}$C] proline CPM** | [$^{3}$H] Tymidine CPM** mean ± SEM* | Proteins Synthesize |
|---|---|---|---|---|---|
| *plastic | 511 ± 91 | 787 ± 70 | 1298 | 500 ± 34 | type I procollagen + collagen + procollagen intermediates |
| collagen sponge | 279 ± 54 | 430 ± 92 | 709 | 395 ± 48 | |
| collagen sponge + 5% Hyaluronic Acid | 638 ± 31 | 788 ± 31 | 1426 | 595 ± 21 | |
| collagen sponge + 1% Fibronectin | 638 ± 32 | 731 ± 70 | 1369 | 600 ± 6 | |

*SEM = standard error of mean
**CPM = counts per minute incorporated

TABLE 3

Morphological Results of Epidermal Cell Cultures

| Substrate | Observations |
|---|---|
| plastic | 1. Stratified into a few loose layers<br>2. no evidence of basement membrane formation |
| collagen sponge | 1. cells grow into several stratified layers on sponge surface<br>2. some cultures show evidence of a basement membrane-like structure<br>3. in interior, cells form clusters of cuboidal cells that contain intracellularly accumulations of a lipid-like substance |

TABLE 4

[$^{14}$C] Proline and [$^{3}$H] Thymidine Incorporation Into Epidermal Cells**

| | [$^{14}$] Proline CPM* substrate medium | | [$^{3}$H] Thymidine CPM* substrate |
|---|---|---|---|
| Substrate | mean ± SEM+ | mean ± SEM+ | mean ± SEM+ |
| plastic | 245 ± 42 | 422 ± 86 | 880 ± 25 |
| collagen | 247 ± 58 | 529 ± 64 | 525 ± 21 |

*cells were labeled for 4 hours; CPM = counts per minute (incorporated)
**values shown are averages obtained for cells grown in culture for 15 to 20 days
+ SEM = standard error of mean

EXAMPLE 1

General Protocol for Purification of Bovine Hide Collagen. Insoluble collagen was extracted from cattle hide as follows.

One liter of frozen raw cowhide was defrosted at room temperature and placed into a processing tank of a capacity of 18 liters. The tank was equipped with air and water lines.

Distilled water was added until the total volume of the processing mixture reached 14 liters. Air at a pressure of 6 psi was introduced into the tank for 5 minutes to create a homogenous mixture. This mixture then was left to sediment for 20 minutes. After complete sedimentation occurred the liquid phase was drained and fresh distilled water was added until the total volume reached 14 liters. This procedure was repeated three times.

Eight liters of 99.8% isopropanol were added to the solid phase; the mixture was air mixed and the tank was placed on gyrotory shaker for 12 hours.

The liquid phase was removed and 8 liters of 99.8% isopropanol was mixed with solid phase. The mixture then was placed on a shaker for another 12 hours.

After removing the liquid phase, the material was washed with two liters of distilled water, poured into plastic trays and then placed into a freezer until frozen solid. The frozen material was then placed in the cold trap of a freeze dryer with the shelf maintained at 0° C. A vacuum of 10 microns was then applied for 48-96 hours. The vacuum was then released and material removed.

Collagen was identified by standard procedure, such as by sodium dodecyl sulfate polyacrylamide gel electrophoresis and amino acid analysis as typical of type I collagen free of noncollageneous protein contamination.

EXAMPLE 2

A collagen flake product of the invention is prepared as follows.

A collagen dispersion is prepared in the following manner. A 1N solution of HCL is slowly added added to 120 ml of distilled water until the pH is 3.0 at room temperature. The contents of the beaker are then emptied into a 200 ml graduated cylinder.

1.2 grams of purified (according to example 1) insoluble collagen obtained from Devro, INC., Somerville, N.J. is added to a Waring blender along with the 120 ml of HCl at pH 3.0. The 1% of W/V dispersion is blended at high speed (5,000 rpm) for 3 minutes.

The dispersion is emptied into a sidearm flask (600 ml). A vacuum of 100 microns is applied to the dispersion at room temperatures until the air bubbles are removed. This procedure may require up to 15 minutes. One liter of the 1% V/W collagen dispersion is poured into a 10"×20"×1" tray and frozen at −30° C. and freeze-dried.

A 3"×3" by ¼" piece of freeze dried collagen sponge is crosslinked by heating to −110° C. in a vacuum for 72 hours followed by exposure to aqueous vapors of a 10% solution of cyanamide for 24 hours.

Crosslinked freeze-dried collagen sponge is placed in a Waring blender and blended for 5 minutes at low speed (3,000 rpm). Flakes of collagen are formed.

The collagen flakes are about 1 mm in thickness and 1 mm to 1 cm in length and width. Pore sizes range from 100 to 10,000 um.

1 g of collagen flakes is sealed in a plastic bag and sterilized by exposure to 2.5 M rads gamma radiation.

The collagen flake product is ready for treating patients suffering from decubitus ulcers which exhibit dermal erosion and loss of epidermis.

EXAMPLE 3

Patients suffering of pressure sores known as decubitus ulcers were treated by the conventional protocol which included daily irrigation of the wound and gauze bandaging. No decrease in wound area over a six week period is observed.

In many cases the wound area remained constant for three or more months.

The protocol for treatment of patients was modified as follows. The nurses pack the wound and cover the edges of surrounding skin with the collagen flakes (removed from the plastic bag) until the flake level was approximately level with wound. The collagen flaked packed wound is then bandaged with gauze. After 1 day the packing of collagen flake is removed, the wound is washed and irrigated with saline. It is observed that not all of the collagen flake product is removed but there is evidence of cellular ingrowth which remains in the wound, especially on the bottom. The wound is repacked with a fresh supply of collagen flake.

The procedure is repeated on a daily basis for six to twelve weeks. Gradually it is observed that the capillaries at the base of the wound turn gradually from a very pale cream color to a pale pink and reddish color indicating the development of vasculature and initiation of some blood circulation.

It is also noted that the flap near the edge of the wound typical of decubitus ulcers, gradually starts adhering and forming new tissue joining it to the surrounding edges of the wound, thus gradually closing the wound.

New tissue growth evidenced by a tissue of a ligth pink color is also noticed around the wound.

Depending on the seriousness of the patient's wound condition, the wound is gradually closed by new ingrowth of tissue gradually starting from the bottom and the side and invading the cavity of the wound. At the end of the treatment the new tissue has essentially filled the wound.

The wound is then ready for grafting-on tissue such as by autograft. When required an epidermal growth factor is added.

Several packages of the flake product can be used for wound packing. Each package can contain different amounts of the flake product.

FIGS. 1A, 1B and 1C show the gradually closing of a severe decubitus ulcer as a result of treatment with the collagen flake product of the invention. In photograph C, taken after 1½ months, it is noted that the color of the newly grown tissue has assumed a pinkish light color symptomatic of increased blood circulation and the formation of capillaries.

The flake product not only absorbs the fluid due to the edema but also absorbs the bacteria in the wound.

The flake product can be used in conjunction with a collagen sponge. The wound is first packed with the flakes (especially in the difficult to reach parts), then the sponge placed on top, followed by an occlusive dressing.

The flake product of the invention is useful also for treatment of internal wounds, as in liver surgery. In general the collagen product is believed to stimulate blood clotting, platelet aggregation (through ADP release), and to attract white cells into the collagen fibrous structure. The cell migrate through the pores and as they are filled, the cells attach themselves to the collagen fibers. Then an extracellular (connective tissue) is formed. The matrix is gradually disintegrated, and endothelial cells extend forming new capillaries. Thus the new tissue is reconstituted. Depending on various factors, the open wounds can be gradually closed in 7-14 days and thus a new implant will be developed.

EXAMPLE 4

The preparation of collagen sponge with a moisture vapor barrier is carried out as follows.

Insoluble collagen (1.2 g) is added to 120 ml of dilute HCL solution pH 3.0 and the mixture is dispersed in a Waring Blender at 2,000 RPM for 1 minute. The dispersion is then poured into a vacuum flask and deaerated at a vacuum of less than 10 mtorr for 10 minutes. Deaerated collagen dispersion is then colled to 0° C., frozen at −30° C., and freeze dried at a vacuum of less than 10 mtorr. A 1 mm layer of Silastic Medical Grade adhesive is applied to the surface of the collagen sponge using a spatula. The Silastic diffusion control layer is cured by application of a vacuum of 100 mtorr for a period of 2 hours at 22° C. The resultant complex of the diffusion control and sponge layers are placed sponge side down on the wound.

Treatment of the wound is carried out as described above. The invention has been described for one skilled in the art and variations can readily be performed without departing from the spirit of the invention.

The publications listed below are of interest as background for the invention.

PUBLICATIONS IN THIS FIELD WHICH ARE OF INTEREST ARE THE FOLLOWING

U.S. Patents

Patent No. 3,098,693 - SHEENAN
Patent No. 3,800,792 - MCKNIGHT
Patent No. 3,903,882 - AUGURT
Patent No. 3,955,012 - OKANURA
Patent No. 4,060,081 - YANNAS
Patent No. 4,280,954 - YANNAS
Patent No. 4,350,629 - YANNAS
Patent No. 4,352,883 - LIM
Patent No. 4,363,758 - MASUHO
Patent No. 4,374,121 - CIOCA
Patent No. 4,399,123 - OLIVER
Patent No. 4,409,322 - JEFFERIES
Patent No. 4,412,947 - CIOCA
Patent No. 4,418,691 - YANNAS
Patent No. 4,458,678 - YANNAS

German Patents

Patent No. 2734 503 - FREUDEN BERG

ARTICLES (1) ALBERT L. RUSIN, M.D., KURT H. STENZEL, M.D, TERUO MIYATA, Ph.D., MARY JO WHITE, B.S., and MICHAEL DUNN, M.D. New York, N.Y. Collagen as a Vehicle for Drug Delivery, *The Journal of Clincal Pharmacology*, (August–September, 1973).

(2) DOILLON, C. J., DUNN, M. G., Berg, R. A. AND SILVER, F. H. (1985) Collagen Deposition During Wound Repair. *Scanning Electron*, June 24, 1985, *Microscopy II:* 897–903.

(3) DOILLON, C. J. and SILVER, F. H. (1986a) Collagen-based Dressing: Effects of Hyaluronic Acid and Fibronectin. *Biomaterials* 7:3:7.

(4) DOILLON, C. J., SILVER, F. H. and BERG, R. A. (May, 1987) Fibroblast Growth on a Porous Collagen Sponge Containing Hyaluronic Acid and Fibronectin. *Biomaterials* 8,195–200.

(5) DOILLON, C. J., WHYNE, C. F., BRANDWEIN, S. and SILVER, F. H. (1986) Collagen-based Wound Dressings: Control of the Pore Structure and Morphology. *J. Biomed. Mat. Res.* 20:1219–1228.

(6) DOILLON, C. J., WASSERMAN, A. J., BERG, R. A. and SILVER, F. H. (1986), Epidermal Cells Cultured on a Collagen-based material. Electron Microscopic Society of America, San Francisco Press, Inc. San Francisco, Calif., 212–213.

(7) F. H. SILVER, I. V. YANNAS, and E. W. SALZMAN, In Vitro Blood Compatibility of Glycosaminoglycan-Precipitated Collagens, *Journal of Biomedical Materials Research*, Vol. 13,701–716 (1979).

(8) FREDERICK H. SILVER, IOANNIS V. YANNAS, and EDWIN W. SALZAN, Glycosaminoglycan Inhibition of Collagen Induced Platelet Aggregation, *Thrombosis Research*, Vol. 13 No. 2, pp. 267–277.

(9) JAMES M. PACHENCE, RICHARD A. BERG, and FREDERICK H. SILVER, Collagen: Its Place in the Medical Device Industry, *The Biomaterials Center.* MD & Dl, January, 1987.

(10) KEVIN WEADOCK, ROBERT M. OLSON, and FREDERICK H. SILVER, Evaluation of Collagen Cross-linking techniques, *Biomat., Med. Dev., Art. Org.*, 11(4), 293–318 (1983–84)

(11) ROBERT A. FULLER and JONATHAN J. ROSEN, Materials for Medicine, October, 1986, *Scientific American*

(12) Synthetic Skin Ready To Try On Humans; *Chemical & Engineering News,* October 4, 1965

(13) Alexander, S. A. and Donoff, R. B. (1980) The glycosaminoglycans of open wounds. *J. Surg. Res.* 29: 422–429.

(14) AZIZKHAN, R. G., AZIZKHAN, J. C., ZEFFER, B. R. and FOLKMAN, J. (1980) Mast cell heparin stimulates migration of capillary endothelial cells in vitro. *J. Exp. Med.* 152, 931–944.

(15) BROKAW, J., DOILLON, C. J., HAHN, R. A., BIRK, D. E., BERG, R. A. and SILVER, F. H. (1985) *Intl. J. Biological Macromolecules* 7,135–140.

(16) DAVIDSON, J. M., KLAGSBRUN, M., HILL, K. E., BUCKLEY, A., SULLIVAN, R., BREWER, P. S. and WOODWARD, S. C. (1985) *J. Cell Biology* 100: 1219–1227.

(17) DOILLON, C. J. WHYNE, C. F., BERG, R. A., OLSON, R. M. and SILVER, F. H. (1984) Fibroblast - collagen sponge interactions and especial deposition of newly synthesized collagen fibers in vitro and in vivo. *Scanning Electron Microscopy III:* 1313–1320.

(18) DUNN, G. A. and EBENDAL, T. (1978) Contact guidance on oriented collagen gels. *Exp. Cell Res.* 111, 475–479.

(19) FORRESTER, J. C., HUNT, T. K., HAYES, T. L. and PEASE, R. F. (1969) Scanning electron microscopy of healing wounds. Nature 221, 373–374.

(20) GAUSS-MULLER, V., LEINMAN, H. K., MARTIN, G. R. and SCHIFFMAN, E. (1980) Role of attachment factors and attractants in fibroblast chemotaxis. *J. Lab. Clin. Med.* 96, 1071–1080.

(21) GIBSON, W. T., COUCHMAN, J. R. and WEAVER, A. C. (1983) Fibronectin distribution during the development of fetal rat skin. *J. Invest. Dermatol.* 81, 480–485.

(22) GOSPODAROWICZ, D. and Ill, C. R. (1980) The extracellular matrix and control of proliferation of corneal and lens epithelial cells. *Exp. Eye Res.* 31, 181–199.

(23) GRINNELL, F., BILLINGHAM, R. E. and BURGESS, L. (1981) Distribution of fibronectin during wound healing in vivo. *J. Invest. Dermatol.* 76, 181–189.

(24) GRINNELL, F. and BENNETT, M. H. (1982) Ultrastructural studies of cell-collagen interactions. *Meth. Enz.* 82, 535–544.

(25) HELDIN, C. H., WESTERMARK, B. and WASTESON, A. (1981) Platelet-derived growth factor. *Biochem. J.* 193, 907–913.

(26) KAO, W. W. Y., BERG, R. A. and PROCKOP, D. J. (1975) Ascorbate increases the synthesis of procollagen hydroxyproline by cultured fibroblasts from chick embryo tendons without activation of prolylhydroxylase. *Biochem, Biophys.* Acta. 411, 202–215.

(27) KAO, W. W. Y., BERG, R. A. and PROCKOP, D. J. (1977) Kinetics for the secretion of procollagen from freshly isolated tendon cells. *J. Biol. Chem* 252: 8391–8397.

(28) KLEINMAN, H. K., KLEBE R. J. and MARTIN, G. R. (1981) Role of collagenous matrices in the adhesion and growth of cells. *J. Biol.* 88, 473–485.

(29) KLEINMAN, H. K. WILKES, C. M. and MARTIN, G. R., Interaction of fibronectin with collagen fibrils, *Biochemistry* 1981, 20, 2325–2328.

(30) OLIVER, R. F., BARKER, H., COOKE, A. and GRANTS, R. A. Dermal collagen implants, *Biomaterials* 1982, 3, 38–40.

(31) PEACOCK E. E. (1984) Collagenolysis and the biochemistry of wound healing, in Wound Repair, edited by E. E. Peacock, 3rd edition, W. B. Saunders Co., Philadelphia, pp. 102–140.

(32) RUOSLAHTI, E., HAYMAN, E. G., PIERSCHBACHER, M. and ENGVALL, E. (1982) Fibronectin: purification, immunochemical properties and biological activities. *Methods Enzymology* 82, 803–831.

(33) TASSIN, J., JACQUEMIN, E. and COURTOIS, Y. (1983) Interaction of Bovine Epithelial Lens (BEL) Cells with

(34) THOMASECK, J. T., HAY, E. D. and FUJIWARD, K. (1982) Collagen modulates, cell shape and cytoskeleton of embryonic corneal and fibroma fibroblasts: distribution of actin, -actinin and myosin. *Dev. Biol.* 92: 107–122.

We claim:

1. A collagen product comprising a porous mass of slices of porous collagen fibers, the porous mass having a dualtype porosity of channels and pores in which the channels form a labyrinthal-type structure extending between the slices and individual fibers, with some channels extending throughout the product, and in which the pores are contained in the fibers.

2. The collagen product of claim 1 which is dimensionally stable but wherein the slices are slidable with respect to each other.

3. The collagen product of claim 1 which is a cross-linked collagen.

4. The collagen product of claim 1 which is a collagen which is not cross-linked.

5. The collagen product of claim 1 which is dehydrated.

6. The collagen product of claim 5 which has a moisture content not exceeding about 15% by weight.

7. The collagen product of claim 5 which is sterile.

8. The sterile collagen product of claim 7 wherein the collagen product is sealed in a plastic bag.

9. A wound dressing especially for decubitus ulcers which comprises a moisture vapor diffusion layer and the collagen product of claim 1.

10. A therapeutic method for treatment of wounds of a patient which comprises packing the wound with a porous mass of slices of porous collagen fibers, the porous mass having dual-type porosity of channels and pores in which the channels extend between the slices and individual fibers, with some channels extending throughout the product, and in which the pores are contained in the fibers, whereby the healing of the wound is promoted by fibroblast movement into the channels and pores, attachment of collagen inside the channels and new tissue is formed in the wound.

11. The therapeutic method of claim 10 wherein the packing of the wound is carried out periodically.

12. The therapeutic method of claim 10 wherein the wound is a pressure wound.

13. The therapeutic method of claim 12 wherein the wound is an ulcer.

14. The therapeutic method of claim 13 wherein the ulcer is a stage 2 or 3 ulcer.

15. The therapeutic method of claim 14 wherein the ulcer is decubitus ulcer.

16. A process for making a collagen product of a porous mass of slices of porous collagen fibers, the porous mass having a dual-type porosity of channels and pores in which the channels extend between the slices and individual fibers, with some channels extending throughout the product, and in which the pores are contained in the fiber said process comprising shearing a biodegradable collagen porous sponge-like material into slices while minimizing application of pressure on the sponge-like product during shearing, and separating the slices, thereby forming the mass of slices.

17. The process of claim 16 wherein the sponge-like material is a sponge.

18. The process of claim 16 wherein the shearing process is carried out concurrently with, prior to, or following cross-linking of the sponge-like material.

19. The process of claim 16 wherein the shearing process is carried out at a temperature range from about 1° to about 60° C.

20. The process of claim 16 wherein the shearing process is carried out at a temperature of about 20° C.

21. The process of claim 16 wherein the shearing process is carried out under atmospheric conditions.

22. The process of claim 16 wherein the shearing process is carried out under a vacuum.

23. The process of claim 16 wherein the shearing process is carried out in dry air.

* * * * *